US009011895B2

(12) United States Patent
Dai et al.

(10) Patent No.: US 9,011,895 B2
(45) Date of Patent: *Apr. 21, 2015

(54) EB MATRIX PRODUCTION FROM ANIMAL TISSUE AND ITS USE FOR TISSUE REPAIR

(75) Inventors: Jianwu Dai, Boston, MA (US); Eugene Bell, Boston, MA (US); Vladimir Russakovsky, Boston, MA (US)

(73) Assignee: TEI Biosciences, Inc., Boston, MA (US)

( * ) Notice: Subject to any disclaimer, the term of this patent is extended or adjusted under 35 U.S.C. 154(b) by 458 days.

This patent is subject to a terminal disclaimer.

(21) Appl. No.: 12/273,143

(22) Filed: Nov. 18, 2008

(65) Prior Publication Data

US 2009/0162452 A1 Jun. 25, 2009

Related U.S. Application Data

(63) Continuation of application No. 10/884,487, filed on Jul. 2, 2004, now abandoned, which is a continuation of application No. 09/996,640, filed on Nov. 28, 2001, now abandoned, which is a continuation-in-part of application No. 09/871,518, filed on May 31, 2001, now Pat. No. 6,696,074.

(51) Int. Cl.
*A01N 1/00* (2006.01)
*A01N 1/02* (2006.01)
*C12N 5/00* (2006.01)
*C12N 5/02* (2006.01)
*C12N 11/02* (2006.01)
*C12N 11/08* (2006.01)
*A61L 27/36* (2006.01)
*A61L 27/38* (2006.01)
*A61K 35/44* (2006.01)
*A61K 38/18* (2006.01)

(52) U.S. Cl.
CPC .......... *A61L 27/3683* (2013.01); *A61L 27/3604* (2013.01); *A61L 27/3625* (2013.01); *A61L 27/3687* (2013.01); *A61L 27/3691* (2013.01); *A61L 27/3834* (2013.01); *A61L 2430/40* (2013.01); *A61K 35/44* (2013.01); *A61K 38/1875* (2013.01)

(58) Field of Classification Search
CPC ............ A61L 27/3691; A61L 2430/40; A61L 27/3604; A61L 27/362; A61L 27/3625; A61L 27/3683; A61L 27/3687; A61L 27/3834; A61K 35/34; A61K 35/44; C12N 2502/02; C12N 25/0214; C12N 2533/50; C12N 2533/54; C12N 5/065
See application file for complete search history.

(56) References Cited

U.S. PATENT DOCUMENTS

| 4,801,299 | A | 1/1989 | Brendel |
| 5,336,616 | A | 8/1994 | Livesey |
| 5,624,463 | A | 4/1997 | Stone |
| 5,709,934 | A * | 1/1998 | Bell et al. .................. 428/305.5 |
| 5,756,678 | A | 5/1998 | Shenoy |
| 5,779,960 | A | 7/1998 | Berlowitz-Tarrant et al. |
| 5,916,265 | A | 6/1999 | Hu |
| 5,989,431 | A | 11/1999 | Evans et al. |
| 5,997,895 | A | 12/1999 | Narotam |
| 6,179,872 | B1 | 1/2001 | Bell et al. |
| 6,696,074 | B2 | 2/2004 | Dai et al. |

FOREIGN PATENT DOCUMENTS

WO WO 99/47188 * 9/1998 ............. A61L 31/00

* cited by examiner

*Primary Examiner* — Debbie K Ware
(74) *Attorney, Agent, or Firm* — Fish & Richardson P.C.

(57) ABSTRACT

A method of forming and preserving a bioremodelable, biopolymer scaffold material by subjecting animal tissue to chemical and mechanical processing. In addition to skin tissue, another source of EBM is a blood vessel. EBM may be used for hernia repair, colon, rectal, vaginal and or urethral prolapse treatment; pelvic floor reconstruction; muscle flap reinforcement; lung tissue support; rotator cuff repair or replacement; periosteum replacement; dura repair; pericardial membrane repair; soft tissue augmentation; intervertebral disk repair; and periodontal repair. EBM may also be used as a urethral sling, laminectomy barrier or spinal fusion device.

6 Claims, No Drawings

EB MATRIX PRODUCTION FROM ANIMAL TISSUE AND ITS USE FOR TISSUE REPAIR

CROSS-REFERENCE TO RELATED APPLICATIONS

This application is a continuation of U.S. application Ser. No. 10/884,487, filed Jul. 2, 2004 now abandoned, which is a continuation of U.S. application Ser. No. 09/996,640, filed Nov. 28, 2001 now abandoned, which is a continuation-in-part of U.S. application Ser. No. 09/871,518, filed May 31, 2001 now U.S. Pat. No. 6,696,074, the entire contents of which are incorporated by reference.

BACKGROUND OF THE INVENTION

1. Field of the Invention

This invention relates to the field of tissue engineering, and in particular to animal-derived, bioremodelable, biopolymer scaffold materials used to repair animal tissue. The term "bioremodelable" or "bioremodelability" refers to a material that lends itself to the breakdown by cells that occupy it and use it as a template for creating a replacement made up mainly of newly synthesized components secreted by the cells.

Rebuilding the human body is a significant industry. Human tissue banks and synthetic polymers do not meet the need for repair or replacement of body parts. High on the list of alternative sources of material used to meet this need are animal tissues prepared in new ways that reduce their immunogenicity and maximize their usefulness and efficacy.

In the field of tissue engineering, the following three components are used alone or in combination to repair or create new tissue and organ substitutes, 1) scaffolds made of naturally-occurring polymers (e.g. collagens), man-made polymers, (e.g. PTFE, Dacron, PET or polyethylene) or sell-degrading, man-made polymers (e.g. PLA or PGA); 2) signaling molecules that give developmental instructions to cells; and 3) cells.

Man-made implant materials such as synthetic polymers, plastics, and surface-coated metals may have different degrees of immunogenicity and suffer from significant limitations that prohibit their broad applications. A major limitation is that cells cannot remodel them after implantation. They are highly susceptible to microbial infection, and some undergo calcification. Synthetic vascular conduits have a high incidence of occlusion after peripheral vascular bypass procedures.

2. Description of the Related Art

Several methods of preserving collagen-based matrices from animal tissues have been developed over the last decade (U.S. Pat. No. 4,801,299, issued Jan. 31, 1999; U.S. Pat. No. 5,336,616, issued Aug. 9, 1994; U.S. Pat. No. 5,756,678, issued; U.S. Pat. No. 5,916,265, issued Jun. 24, 1999; and U.S. Pat. No. 5,997,895, issued Dec. 7, 1999). All the methods include a chemical step that either kills or eliminates cells. Since tissues from post-natal animals or humans are the principal materials processed, a fixation step using glutaraldehyde or a similar agent may be used to mask antigenic determinants, eliminate the microbial burden and increase strength. However, aldehydic processing effectively destroys any biological activity, such as cell binding sites, associated with the original tissue and greatly reduces or eliminates the ability of cells to attach to it. It also eliminates binding sites for cell-synthesized products which attach to cells or to intermediates able to bind to cells and cell products that make up the extracellular matrix by cells.

Collagen-based devices that are animal-derived and fixed with glutaraldehyde or a similar agent can not be remodeled since they are highly resistant to metalloproteinase enzymes. The methods suggested in U.S. Pat. No. 4,801,299 and U.S. Pat. No. 5,916,265 include the use of glutaraldehyde or a similar agent for the fixation of tissue derived from a post-natal animal source; the resulting products can not be faithfully remodeled. Glutaraldehyde-treated devices are known to undergo gradual calcification. Heart valves made from fixed animal tissues can require replacement in 5-7 years or sooner due to calcification.

While detergents or sodium hydroxide may be used to process post-natal animal tissue (U.S. Pat. No. 4,801,299, U.S. Pat. No. 5,336,616, U.S. Pat. No. 5,756,678, U.S. Pat. No. 5,916,265, U.S. Pat. No. 5,997,895), they have not been used to process fetal or neo-natal animal tissue as used in U.S. application Ser. No. 09/871,518, referred to herein. For example, U.S. Pat. No. 5,997,895, filed Apr. 30, 1998, provides a certified collagen dura substitute derived from post-natal animal tissue that undergoes an alkaline/salt treatment involving sodium hydroxide and sodium sulfate (preferably in an aqueous solution of 5% sodium hydroxide and 20% sodium sulfate). A method for processing collagen containing materials which uses 1.0 N sodium hydroxide was disclosed in a journal article in 1989 by Diringer H. and Braig H. R. (Diringer H. and Braig H. R., 1989, Infectivity of unconventional viruses in dura mater. The Lancet, 439-440). This reference was cited in the FDA's *Guide for 510(k) Review of Process Dura Mater* (1990, 2).

BRIEF SUMMARY OF THE INVENTION

EBM is a bioremodelable, biopolymer scaffold material derived from fetal, neo-natal or post-natal animal tissue. EBM is processed in a way that preserves its tissue strength without reducing its intrinsic biological properties or compromising the ability of cells that occupy the tissue to remodel it.

Upon processing EBM, binding sites for cells and cell-secreted products that make up the extracellular matrix surrounding cells that occupy it are preserved. Undesirable tissue components of EBM (e.g., DNA, RNA) are solubulized and expressed mechanically from the tissue, and delipidyzing organic solvents are used to reduce the presence of cell and nuclear membranes.

EBM does not calcify, making it safe for use in the human body for repair of soft tissues. EBM can be used as a scaffold for bone repair if treated with an appropriate growth factor(s), if seeded with bone precursor cells or if occupied by bone forming cells when implanted.

EBM may be used as a tissue-building component with or without cells for creating human body replacements. It can be used after the addition of signaling molecules, which will further promote tissue repair. It can also be implanted after stem or differentiated cells are seeded into or onto it.

DETAILED DESCRIPTION OF THE INVENTION

A naturally occurring, biopolymer-based matrix (EBM) is produced from animal tissue by a method comprising the following steps: (1) removing the tissue from its source; (2) optionally extracting growth and differentiation factors from the tissue; (3) inactivating infective agents of the tissue; (4) mechanically expressing undesirable components from the tissue; (5) washing the tissue for removal of chemical residues; (6) optionally drying; and (7) optionally cross-linking the tissue after chemical and mechanical treatment; and (8) optionally terminally sterilizing.

The term "inactivating" or inactivated" refers to the reduction of the concentrations of infective agents (e.g., bacteria, molds, viruses and prions) by 4, 6 or 8 logs consistent with the requirements needed to insure against infectivity. The phrase "mechanically expressing" refers to mechanically applying the necessary pressure to express undesirable components from the tissue. With the aid of appropriate solvents, unwanted components from the product that are potentially antigenic (e.g., DNA, RNA) or other molecules released by reagents (e.g., NaOH) are removed.

In the preferred embodiment, fetal or neo-natal animal tissue is used. One preferred source is fetal bovine tissue between 10 weeks of age and newborn age. As an example, fetal bovine skin is used. Other source material include blood vessels, other tubular structures, internal organs including the bladder, tendons, ligaments, cartilage, membranes such as the kidney capsule or diaphragm, or hard tissues such as cartilage or bone.

EBM made from skin tissues can be used as a skin wound dressing or a skin replacement tissue. With or without the addition of signaling molecules and cells, EBM promotes wound healing. EBM is suitable for the treatment of chronic topical wounds such as burns, ulcers, and avulsion injuries. In grafts to host animals, such as rats, to replace full thickness skin wounds, acellular EBM is shown to remodel to replacement skin without scaring. However, secondary derivatives are absent. If seeded with dermal fibroblasts and keratinocytes, EMB can serve as a living skin replacement.

EBM can be used as a repair or replacement device throughout the human body. For example, EBM can be used as a urethral sling or laminectomy barrier because of its high physical strength, resistance to stretch, suturability, cell-compatibility and bioremodelability. EBM may be used for hernia repair, colon, rectal, vaginal and or urethral prolapse treatment; pelvic floor reconstruction; muscle flap reinforcement; lung tissue support; and soft tissue augmentation.

EBM produced from fetal or neo-natal animal skins (e.g., bovine skin) can be used for pericardial, periosteal, rotator cuff, or dura repair or replacement, or for hernia repair. It is drapable and has single suture-pullout strength of more than 20 Newtons.

EBM used as a spinal fusion device can serve as a carrier of growth factors to generate bone. EBM derived from skin has been found to induce bone formation with the addition of rhBMP2 or bone signaling complexes. Meshed EBM enriched with rhBMP2 was implanted subcutaneously in rats. Freeze-dried EBM was soaked in a solution of rhBMP2 (0.1 mg/ml). Histological examination of the implants at two weeks confirmed the induction of bone by enriched EBM. "Signaling complexes" refer to tissue-specific compositions comprising a number of factors necessary to promote cell division, direct patterning, morphogenesis and differentiation of specific cells, tissues and organs. Methods of generating signaling complexes (Signal-plex™) are described in U.S. application Ser. No. 09/901,765, filed Jul. 9, 2001, the entire contents of which are incorporated herein by reference.

EBM can be used to repair the intervertebral disk after disketomy by acting as a barrier to cells surrounding the disk and promoting regeneration of cells within the disk. EBM can be used in periodontal repair by acting as a membrane barrier to specific cell populations and facilitating regeneration of soft tissue and bone.

EBM can be homogenized for use in an injectable form or as a foam as a hemostat, dura replacement, and other similar areas of treatment. The same or similar processing described in the examples above can be applied to non-skin tissues of the body to provide scaffolds of replacement parts with or without the addition of cells, signaling complexes or drugs, with the expectation that if acellular or cellular they will be vascularized and populated with host cells.

This disclosure is not limited to preserving EBM derived from those tissues or organs described herein. EBM may be derived from a wide variety of tissues and organs.

EXAMPLE 1

Preparation of an EBM Blood Vessel

The preferred protocol to prepare EBM derived from a blood vessel is as follows. All of the following steps are performed in a laminar-flow hood using aseptic techniques and sterile solutions.

A blood vessel is cut out from the body of an animal. Flesh is removed from the blood vessel, and the artery is placed on a 4 mm mandrill. Flesh can be removed from the blood vessel using dissection tools, if done by hand; serrated tipped forceps are used to lift the flesh, and curved scissors are used to remove the flesh. Defleshing can also be performed by a defleshing machine. If carried out manually, the process should continue as follows.

The blood vessel is placed in 20% bleach for 30±2 minutes on a rocking platform on ice. The temperature of the bleach is 4±2° C. The volume of the bleach is 500±50 mls in a 1.0 liter square, wide-mouth bottle with a screw cap. The blood vessel is dipped into 1.0 liters of Milli-Q™ water for approximately 5-10 seconds to wash off the bleach.

The blood vessel is placed in a 5.2N solution of NaOH for 30±2 minutes on a rocking platform on ice. The temperature of the NaOH is 4±2° C. The volume of the NaOH is 500±50 mls in a 1.0 liter square, wide-mouth bottle with a screw cap. The blood vessel is dipped 1.0 liters of 0.2 µm filtered Milli-Q™ water for approximately 5-10 seconds to wash off the NaOH. The concentration of NaOH and the time of exposure to the NaOH can be increased or decreased depending upon the thickness of the blood vessel. This is followed by three washes in 1.0 liter of 0.2 µm filtered Milli-Q™ water for up to 20 minutes each.

The blood vessel is transferred into a 1:1 chloroform/ethanol (95%) solution for 5 minutes on a rocking platform. The volume of the solution is 500±50 mls in a 1.0 liter square, wide-mouth bottle with a screw cap.

A terminal sterilization step is optionally performed using either 7.5% hydrogen peroxide, ethylene oxide or gamma radiation. When using hydrogen peroxide as a sterilizing agent, it is necessary to aseptically package the product immediately afterwards. When using ethylene oxide or gamma radiation, the product can be sterilized in a final package.

The blood vessel is washed in 70% ethanol for approximately 10 minutes on a rocking platform. The volume is 1.0 liter in a 1.0 liter square, wide-mouth bottle with a screw cap. To remove ethanol, the blood vessel is washed in 1.0 liter of 0.2 µm filtered Milli-Q™ water for approximately 5 minutes on a rocking platform, and then washed in 1.0 liter of 0.2 µm filtered Milli-Q™ water for 10 minutes.

The blood vessel is immersed in 1.0 liter of sterile PBS (phosphate buffered saline) for 20±4 hours on a rocking platform at a temperature of 4±2° C. The blood vessel may be optionally freeze-dried.

The EBM blood vessel can be enhanced by the addition to it of vascular signaling complexes designed to attract circulating EPS (endothelial precursor cells)—cells able to differentiate into both smooth muscle and endothelial cells.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method for producing and preserving a biopolymer scaffold material, comprising the steps of:
   a. providing a sheet of defleshed animal tissue by removing the flesh from a sample of animal tissue;
   b. treating the sheet of defleshed tissue with NaOH to inactivate infectious agents;
   c. applying pressure to said tissue to remove undesirable components from said tissue;
   d. rinsing said tissue in an aqueous solution
   e. delipidizing said tissue; and
   f. washing said tissue to remove chemical residues.
2. The method of claim 1 wherein said tissue is selected from the group consisting of fetal, neo-natal and post-natal animal tissue.
3. The method of claim 2 wherein said tissue is bovine.
4. The method of claim 2 wherein said tissue is porcine.
5. The method of claim 1 further comprising:
   combining said biopolymer scaffold material with a signaling complex, stem cells or with a drug.
6. The method of claim 1 comprising treating the defleshed animal tissue with hydrogen peroxide at a time after step d.

* * * * *

UNITED STATES PATENT AND TRADEMARK OFFICE
CERTIFICATE OF CORRECTION

PATENT NO.        : 9,011,895 B2                                    Page 1 of 1
APPLICATION NO.   : 12/273143
DATED             : April 21, 2015
INVENTOR(S)       : Jianwu Dai, Eugene Bell and Vladimir Russakovsky It is certified that error appears in the above-identified patent and that said Letters Patent is hereby corrected as shown below:

Title Page, Col. 2, line 5, item (56), delete "and or" and insert -- and/or --

In the Claims

Col. 6, line 7, claim 1, after "solution" insert -- ; --

Signed and Sealed this
First Day of September, 2015

Michelle K. Lee
*Director of the United States Patent and Trademark Office*